United States Patent [19]

Baker

[11] 4,036,958

[45] July 19, 1977

[54] INSECTICIDAL AND MITICIDAL ACTIVE ISOTHIURONIUM TRICYCLOHEXYL TIN IMIDE

[75] Inventor: Don R. Baker, Orinda, Calif.

[73] Assignee: Stauffer Chemical Company, Westport, Conn.

[21] Appl. No.: 619,882

[22] Filed: Oct. 6, 1975

[51] Int. Cl.² .................... A01N 9/00; C07D 209/34
[52] U.S. Cl. ................................ 424/245; 260/326 E
[58] Field of Search ................... 260/326 E; 424/245

[56] References Cited

U.S. PATENT DOCUMENTS 3,544,588  12/1970  Minieri ........................ 260/326 E

OTHER PUBLICATIONS

Chemical Abstracts, vol. 72 (1970), p. 121655n.

*Primary Examiner*—V. D. Turner
*Attorney, Agent, or Firm*—Michael J. Bradley

[57] ABSTRACT

A tricyclohexyl tin imide having the formula

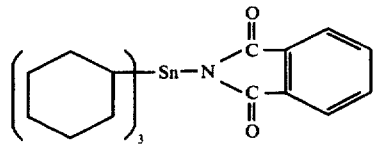

is an active insecticide, miticide and lepidoptericide which can be applied to insects, mites or lepidoptera at any stage of development.

3 Claims, No Drawings

INSECTICIDAL AND MITICIDAL ACTIVE ISOTHIURONIUM TRICYCLOHEXYL TIN IMIDE

DESCRIPTION OF THE INVENTION

The present invention is a novel tricyclohexyl tin imide which is an active insecticide, miticide and lepidoptericide. The compound of the present invention is represented by the formula:

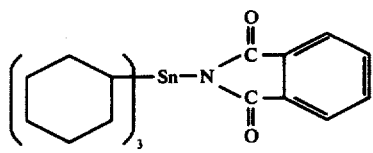

Preparation of the compounds of this invention are illustrated by the following example:

EXAMPLE 1

Preparation of tricyclohexyl Tin Imide - 8.1 g. cyclohexyl tin chloride (0.02 mole), 3.7 g. potassium phthalimide (0.02 mole) and 50 ml dimethlformamide were mixed together in a round-bottom flask equipped with a mechanical stirrer, reflux condenser and thermometer and heated at reflux temperature (143°-145° C.) with stirring for one hour. The reaction mixture was allowed to stand overnight at room temperature and then diluted with 100 ml $H_2O$ and 100 ml $CHCl_3$. The lower organic phase was separated and washed with 100 ml water, then washed with 100 ml saturated $NaHCO_3$ solution, dried over $MgSO_4$ and evaporated under vacuum to give a solid product. The solid was then washed with 50 ml methanol to yield 6 g. of solid having a melting point of 161°-163° C. Spectral evidence (IR and NMR) confirmed the structure of the product.

This compound will be hereinafter referred to as Compound No. 1.

LEPIDOPTERICIDAL EVALUATION

Compound No. 1 was evaluated for lepidoptericidal activity on various lepidopterous species as follows: I. Salt-Marsh Caterpillar [*Estigmene acrea* (Drury)]:

Test compounds are diluted in a 50—50 acetone-water solution. Sections of curly dock (Rumex crispus) leaves, approximately 1×1.5 inches, are immersed in the test solutions for 2-3 seconds and placed on a wire screen to dry. The dried leaves are placed in petri dishes containing a moistened piece of filter paper and infested with five second-instar salt-marsh larvae. Mortality of the larvae is recorded 48 hours later, and a piece of synthetic media is added to dishes containing survivors. These are then held for five additional days to observe for any delayed effects of the test chemicals.

Test concentrations range from 0.05% down to that at which approximately 50% mortality occurs. II. Cabbage Looper [*Trichoplusia ni* (Hübner)]:

Same as the Saltmarsh Caterpillar (I) except that cotyledons of hyzini squash (*Calabacita abobrinha*) are utilized as the host plant rather than curly dock. III. Tobacco Budworm [*Heliothis virescens* (F.)]:

Same as the Saltmarsh Caterpillar (I) except that leaves of Romaine lettuce (*Latuca sativa*) are utilized as the host plant rather than curly dock. IV. Beet Armyworm [*Spodoptera exigua* (Hübner)]:

Same as for the Cabbage Looper (II). V. Two-Spotted Mite [*Tetranychus urticae* (Koch)]:

Pinto bean plants (*Phaseolus sp.*) approximately 10 cm tall, are transplanted into sandy loam soil in 3-inch clay pots and thoroughly infested with two-spotted mites of mixed ages and sexes. Twenty-four hours later, the infested plants are inverted and dipped for 2-3 seconds. In 50—50 acetone-water solutions of the test chemicals. Treated plants are held in the greenhouse, and seven days later mortality is determined for both the adult mites and the nymphs hatching from eggs which were on the plants at the time of treatment. Test concentrations range from 0.05% down to that at which 50% mortality occurs. VI. Contact Residue Assay on the Housefly [*Musca domestica* L.]:

The test compound is diluted in acetone and aliquots are pipetted onto the bottom of 55 × 15 mm aluminum dishes. To insure even spreading of the chemical on the bottom of the dishes, one ml of acetone containing 0.02% peanut oil is also added to each dish. After all solvents have evaporated, the dishes are placed in circular cardboard cages containing 25 female houseflies. The cages are covered on the bottom with cellophane and the top with tulle netting, and each contains a sugar-water saturated cotton plug for maintenance of the flies. Mortality is recorded after 48 hours. Test levels range from 100 ug/25°+ houseflies down to that at which approximately 50% mortality occurs. VII. Direct Spray Assay on Lygus Bug [*Lygus hesperus* (Knight)]:

The test compound is in a 50—50 acetone-water solution. Two cc of the solution is sprayed through a DeVilbiss type EGA hand spray gun into circular cardboard cages containing one string bean pod and ten adult lygus bugs. The test cages are covered on the bottom with cellophane and the top with tulle netting. Percent mortality is recorded 48 hours later. Test concentrations range from 0.05% down to that at which approximately 50% mortality occurs. VIII. Direct Spray Assay on Black Bean Aphid [*Aphis fabae* (Scop.)]:

Nasturtium plants (Tropaeolum sp.), approximately 5 cm tall, are transplanted into sandy loam soil in 3-inch clay pots and infested with 25-50 black bean aphids of mixed ages. Twenty-four hours later, they are sprayed, to the point of runoff, with 50—50 acetone-water solutions of the test chemical. Treated plants are held in the greenhouse and mortality is recorded after 7 days. Test concentrations range from 0.05% down to that at which 50% mortality occurs. IX. Direct Spray Assay on German Cockroach [*Blattella germanica* (Linne)]:

The test compound is diluted in a 50—50 acetone-water solution. Two cc of the solution is sprayed through a DeVilbiss type EGA hand spray gun into circular cardboard cages containing ten one-month-old German cockroach nymphs. The test cages are covered on the bottom with cellophane and the top with tulle netting. Percent mortality is recorded 7 days later. Test concentrations range from 0.1% down to that at which approximately 50% mortality occurs. X. Systemic Tests:

A. Salt-marsh Caterpillar Larvae [*Estigmene acrea* (Drury)]- Test chemicals are dissolved in acetone and aliquots are diluted in 200 cc of water in glass bottles. Two kidney bean plants (*Phaseolus vulgaris*), with expanded primary leaves, are supported in each bottle by cotton plugs so their roots and stems are immersed in the treated water. To each plant is then pinned a small mass of ready-to-hatch salt-marsh caterpillar eggs and the plants are placed in the greenhouse. Mortality is recorded after all control eggs have hatched and the young larvae are feeding on the plants. Test concentrations range from 10 ppm down to that at which approximately 50% mortality of the newly hatched larvae occurs.

B. Two-Spotted Mite [*Tetranchus urticae* (Koch)]: Test chemicals are dissolved in acetone and aliquots are diluted in 200 cc of water in glass bottles. Two pinto bean plants (*Phaseolus sp.*), with expanded primary leaves, are supported in each bottle by cotton plugs, so that their roots and stems are immersed in the treated water. The plants are then infested with 74–100 two-spotted mites of various ages and sexes. One week later, the mortality of the adult mites and nymphs is recorded. Test concentrations range from 10 ppm down to that at which 50% mortality occurs.

C. Systemic Assay on Black Bean Aphid [*Aphis fabae* (Scop.)]: The test chemical is diluted in acetone and aliquots are thoroughly mixed into 500 grams of dry, sandy loam soil. The treated soil is placed in a pint ice cream carton and a nasturtium plant (*Tropaeolum sp.*) approximately 5 cm tall is transplanted into each carton. The plants are then infested with approximately 25 black bean aphids of mixed ages and placed in the greenhouse. Seven days later mortality is recorded. Test concentrations range from 10 ppm down to that at which approximately 50% mortality occurs.

The results by the above test procedures indicate in Table I the effective concentration at which an LD-50 control effect was achieved on the various species of lepidopterans and mites.

sary that it be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition for example, an emulsion, suspension or aerosol spray. While the concentration of the active pesticide in the present compositions can vary within rather wide limits, from about 99.9 to about 0.1% by weight of the composition, ordinarily the pesticide compound will comprise not more than about 15.0% by weight of the compositions. Preferably, however, the pesticide compositions of this invention will be in the form of solutions or suspensions containing about 0.1 to 1.0% by weight of the active pesticide compound.

What is claimed is:

1. The compound having the formula

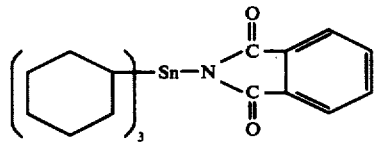

2. A method of controlling insects consisting of applying to the habitat thereof an insecticidally effective

TABLE I

| Compound Number | HF μg/25+* | GR % | LB % | BA % | BASys ppm | 2SM PE % | 2SM Eggs % | 2SM Sys ppm | SMC % | BAW % | TBW % |
|---|---|---|---|---|---|---|---|---|---|---|---|
| 1 | 90 | >.1 | >.05 | .005 | 8 | .0005 | .0008 | >10 | .05 | .01 | >.1 |

HF = Housefly  
GR = German Cockroach  
LB = Lygus Bug  
BA = Black Bean Aphid  
Sys = Systemic  
PE = Post-embryonic  
2SM = Two-Spotted Mite  
SMC = Salt-Marsh Caterpillar  
BAW = Beet Armyworm  
TBW = Tobacco Budworm  
> = greater than  
< = less than The compound of this invention is generally embodied into a form suitable for convenient application. For example, the compound can be embodied into pesticidal compositions which are provided in the form of emulsions, suspensions, solutions, dusts and aerosol sprays. In general, such compositions will contain in addition to the active compound, the adjuvants which are found normally in pesticide preparations. In these compositions, the active compound of this invention can be employed as the sole pesticide component or they can be used in admixture with other compounds having similar utility. The pesticide composition of this invention can contain, as adjuvants, organic solvents, such as sesame oil, xylene range solvents, heavy petroleum, etc; water; emulsifying agents; surface active agents; talc; pyrophyllite; diatomite; gypsum; clays; propellants, such as dichlorodifluoromethane, etc. If desired, however, the active compound can be applied directly to feedstuffs, seeds, etc. upon which the pests feed. When applied in such a manner, it will be advantageous to use a compound which is not volatile. In connection with the activity of the presently disclosed pesticidal compound, it should be fully understood that it is not necesamount of the compound having the formula

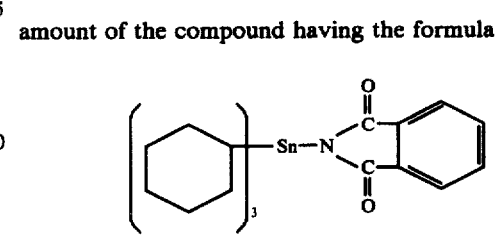

3. A method of controlling mites consisting of applying to the habitat thereof a miticidally effective amount of the compound having the formula

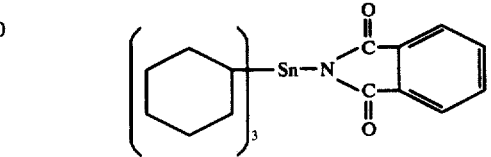

* * * * *